United States Patent [19]

Fisher et al.

[11] 4,156,720

[45] May 29, 1979

[54] CARBOHYDRATE DERIVATIVES OF MILBEMYCIN AND PROCESSES THEREFOR

[75] Inventors: Michael H. Fisher, Bridgewater; Richard L. Tolman, Berkley Heights, both of N.J.

[73] Assignee: Merck & Co., Inc., Rahway, N.J.

[21] Appl. No.: 852,403

[22] Filed: Nov. 17, 1977

Related U.S. Application Data

[63] Continuation-in-part of Ser. No. 786,157, Apr. 11, 1977.

[51] Int. Cl.² .................... A61K 31/70; C07G 11/00
[52] U.S. Cl. .................... 424/180; 536/17 R; 536/4
[58] Field of Search .................... 536/17, 4

[56] References Cited

U.S. PATENT DOCUMENTS

| 3,356,674 | 12/1967 | Ikeda et al. | 536/17 |
| 3,950,360 | 4/1976 | Aoki et al. | 260/343.2 R |
| 3,984,564 | 10/1976 | Aoki et al. | 260/326.34 |

Primary Examiner—Johnnie R. Brown
Assistant Examiner—Blondel Hazel
Attorney, Agent, or Firm—David L. Rose; Harry E. Westlake

[57] ABSTRACT

Carbohydrate derivatives of the antibiotic substance milbemycin, also identified as B-41, and of 13-hydroxy milbemycin are prepared. The carbohydrate groups are attached to the available hydroxy groups of milbemycin and to the hydroxy group synthesized at the 13-position. The reactions may be made selectively such that more than one carbohydrate group may be attached to a single position, or that multiple carbohydrate groups may be attached at different positions on the molecule. The described carbohydrate derivatives have antiparasitic activity.

10 Claims, No Drawings

CARBOHYDRATE DERIVATIVES OF MILBEMYCIN AND PROCESSES THEREFOR

This application is a continuation-in-part of application Ser. No. 786,157, filed Apr. 11, 1977.

BACKGROUND OF THE INVENTION

Milbemycin, or B-41, is a substance which is isolated from the fermentation broth of a milbemycin producing strain of Streptomyces. The microorganism, the fermentation conditions, and the isolation procedures are more fully described in U.S. Pat. No. 3,950,360 and U.S. Pat. No. 3,984,564. The structures of seven of the thirteen milbemycin compounds are described in said patents and the structures of all thirteen compounds are described in the *Journal of Antibiotics* 29 (6) June 1976 pages 76-35 to 76-42 and pages 76-14 to 76-16. The milbemycin compounds described in said patents do not have any carbohydrate groups substituted thereon.

SUMMARY OF THE INVENTION

The carbohydrate derivatives of milbemycin and 13-hydroxy milbemycin are prepared by various procedures, and such compounds have been found to be active antiparasitic agents. Such carbohydrate derivatives are prepared by using one of several reactions. The classical Koenigs-Knorr reaction is successfully employed as are the silver triflate (silver trifluoromethylsulfonate) modification and the Helferich modification, and the reaction utilizing orthoester intermediates. Thus, it is an object of this invention to describe the carbohydrate derivatives of the milbemycin compounds and of the 13-hydroxy milbemycin compounds. A further object is to describe the processes employed to prepare such carbohydrate derivatives. A still further object is to describe the antiparasitic uses of such compounds. Further objects will be apparent from reading the following description.

The milbemycin compounds were originally named as B-41 compounds and given the nomenclature $A_1$, $A_2$, $A_3$, $A_4$, $B_1$, $B_2$, $B_3$, $C_1$ and $C_2$. Later, however, four additional milbemycin compounds were isolated from the fermentation broth and the structures of all thirteen compounds determined. The series was then named as milbemycin and the nomenclature was changed to $\alpha_1$ to $\alpha_{10}$ and $\beta_1$ to $\beta_3$, recognizing the two basic structural differences between the two series of compounds. The following structural formulae and tables fully describes the milbemcyin compounds and the relationship between the old and new nomenclature.

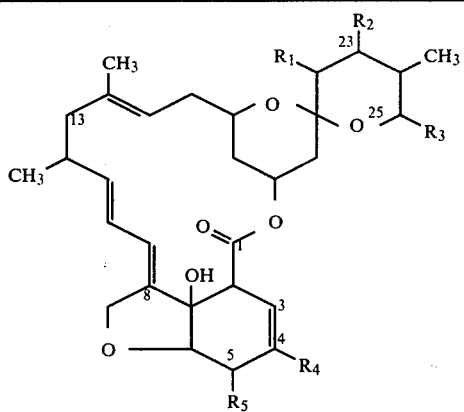

| Milbemycin | $R_1$ | $R_2$ | $R_3$ | $R_4$ | $R_5$ | B-41 |
|---|---|---|---|---|---|---|
| $\alpha_1$ | H | H | $CH_3$ | $CH_3$ | —OH | A3 |
| $\alpha_2$ | H | H | $CH_3$ | $CH_3$ | —$OCH_3$ | B2 |
| $\alpha_3$ | H | H | $C_2H_5$ | $CH_3$ | —OH | A4 |
| $\alpha_4$ | H | H | $C_2H_5$ | $CH_3$ | —$OCH_3$ | B3 |
| $\alpha_5$ | —OH | —OC(O)—CH($CH_3$)—$C_4H_9$ | $CH_3$ | $CH_3$ | —OH | A2 |
| $\alpha_6$ | —OH | —OC(O)—CH($CH_3$)—$C_4H_9$ | $CH_3$ | $CH_3$ | —$OCH_3$ | B1 |
| $\alpha_7$ | —OH | —OC(O)—CH($CH_3$)—$C_4H_9$ | $C_2H_5$ | $CH_3$ | —OH | |
| $\alpha_8$ | —OH | —OC(O)—CH($CH_3$)—$C_4H_9$ | $C_2H_5$ | $CH_3$ | —$OCH_3$ | |
| $\alpha_9$ | H | H | $CH_3$ | —$CH_2$—O—C(O)-(pyrrole-NH) | —OH | C1 |
| $\alpha_{10}$ | H | H | $C_2H_5$ | —$CH_2$OC(O)-(pyrrole-NH) | —OH | C2 |

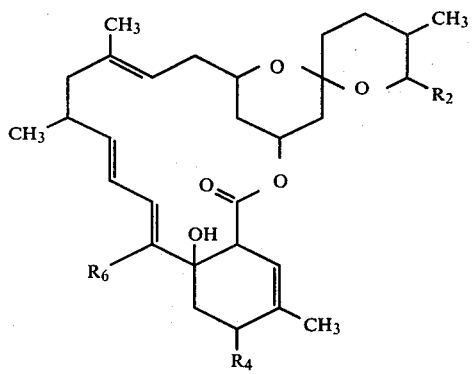

| Milbemycin | $R_2$ | $R_4$ | $R_6$ | B-41 |
|---|---|---|---|---|
| $\beta_1$ | $CH_3$ | $-OCH_3$ | $-CH_2OH$ | A1 |
| $\beta_2$ | $C_2H_5$ | $-OCH_3$ | $-CH_2OH$ | |
| $\beta_3$ | $CH_3$ | $-OH$ | $-CH_3$ | |

The 13- hydroxy milbemycin compounds may be prepared from the milbemycin compounds which are unsubstituted at the 13-position by allylic bromination with N-bromosuccinimide followed by treatment with an alkali metal alkanoate such as sodium acetate, and finally by removing the alkanoyl group by hydrolysis. This process affords the 13-hydroxy group which is then available for substitution with the below described carbohydrate groups.

In the above formulae, at various times, there are found hydroxy groups at the 5, 13 and 22 positions and on the methyl group at the 8 position of formula II. Any one or more of these hydroxy groups may be substituted with a carbohydrate, or sugar moiety (also known as a glycosyl group) to form the compounds of this invention. Such compounds are more precisely defined in the following forulae:

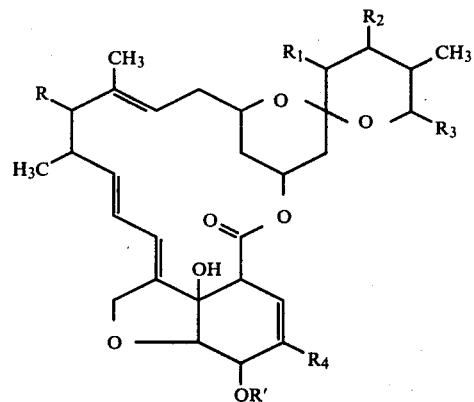

wherein R is hydrogen or a sugar (glycosyloxy) moiety and $R_1$, $R_2$, $R_3$, $R_4$ and $R'$ are defined as follows:

| $R_1$ | $R_2$ | $R_3$ | $R_4$ | $R'$ |
|---|---|---|---|---|
| H | H | $CH_3$ | $CH_3$ | H or sugar |
| H | H | $CH_3$ | $CH_3$ | $CH_3$ |
| H | H | $C_2H_5$ | $CH_3$ | H or sugar |
| H | H | $C_2H_5$ | $CH_3$ | $CH_3$ |
| —OH or sugar | $-O-\overset{O}{\underset{\|}{C}}-\overset{CH_3}{\underset{\|}{C}}HC_4H_9$ | $CH_3$ | $CH_3$ | H or sugar |
| —OH or sugar | $-O-\overset{O}{\underset{\|}{C}}-\overset{CH_3}{\underset{\|}{C}}H-C_4H_9$ | $CH_3$ | $CH_3$ | $CH_3$ |
| —OH or sugar | $-O\overset{O}{\underset{\|}{C}}-\overset{CH_3}{\underset{\|}{C}}H-C_4H_9$ | $C_2H_5$ | $CH_3$ | H or sugar |
| —OH or sugar | $-O\overset{O}{\underset{\|}{C}}-\overset{CH_3}{\underset{\|}{C}}H-C_4H_9$ | $C_2H_5$ | $CH_3$ | $CH_3$ |
| H | H | $CH_3$ | $-CH_2O\overset{O}{\underset{\|}{C}}\text{—pyrrole}$ | H or sugar |
| H | H | $CH_3$ | $-CH_2O\overset{O}{\underset{\|}{C}}\text{—pyrrole}$ | H or sugar |

-continued

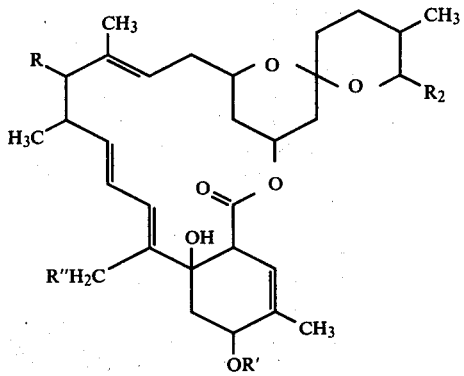

wherein R is hydrogen or a sugar (glycosyloxy) moiety and $R_2$, R' and R" are defined as follows:

| $R_2$ | R' | R" |
|---|---|---|
| $CH_3$ | $CH_3$ | —OH or —O-sugar |
| $C_2H_5$ | $CH_3$ | —OH or —O-sugar |
| $CH_3$ | H or sugar | H | provided that in the first of the above structural formulae at least one of R, $R_1$ and R' is a sugar moiety and in the second of the above structural formulae at least one of R, R', and R" is or contains a sugar moiety.

The nature of the sugar moiety in the above sugar containing groups is not critical and any sugar may be substituted onto the milbemycin substrate using the procedures described below. The preferred sugar moieties are glucopyranosyl, galactopyranosyl, mannopyranosyl, maltosyl, arabinopyranosyl, lyxopyranosyl, xylopyranosyl, ribopyranosyl, oleandrosyl, rhamnopyranosyl, fucopyranosyl, lactosyl, ribofuranosyl, mannofuranosyl, glucofuranosyl, arabinofuranosyl, mycarosyl, cladinosyl, desosaminosyl, daunosaminosyl, mycaminosyl, and the like.

The foregoing sugars are available generally in the D or L configuration. The instant invention includes both of the possible configurations for attachment to the milbemycin substrate.

The above carbohydrate or sugar groups may be substituted on the milbemycin or 13-hydroxy milbemycin compounds as mono, di or tri-saccharides wherein one of the above sugar groups is further substituted with another of the same or different sugar. In addition, where there is more than one hydroxy group available for substitution, the sugar groups may be present on only one or on more than one of such hydroxy groups, and the substitution may be with identical or different sugar moieties.

The preferred sugar substituted are mono- or disaccharide substitution with glucopyranosyl, rhamnopyranosyl, oleandrosyl or daunosaminosyl groups. The most preferred groups are glucopyranosyl and oleandrosyl.

The processes for the substitution of the carbohydrate groups are substituted onto the hydroxy groups of the substrate molecule using the Koenigs-Knorr process, the silver triflate process or the orthoester process.

The carbohydrate starting materials employed for the Koenigs-Knorr, the Helferich modification thereof and the silver triflate processes are protected by acylating all of the free hydroxy groups. The preferred protecting group is the acetyl group, however, other groups such as the benzoate may be employed. The processes for the blocking of the hydroxy groups are well known to those skilled in the art. The acetyl blocking groups are also easily removed at the completion of the reaction by catalytic hydrolysis, preferably base-catalyzed hydrolysis such as with an alcoholic ammonia solution.

The Koenigs-Knorr and silver triflate processes use as starting materials the acetohalosugars such as the appropriate acetobromohexoses and acetobromopentoses of the sugar groups listed above. The bromine atom is substituted on a carbon atom adjacent to an acetyl group and the sugar moiety becomes bonded to the substrate at the carbon atom to which the halogen was attached.

In the Koenigs-Knorr reaction the milbemycin compound is dissolved under anhydrous conditions in an aprotic solvent. Ether is the preferred solvent, however, methylene chloride, acetonitrile, nitromethane, dimethoxy ethane and the like may also be employed. To the substrate solution is added the acetohalosugar and silver oxide. A single molar equivalent of the sugar is required, however, an addition 1 to 3 moles occasionally aids the reactions, however, molar excesses beyond 3 tend to make the isolation of the product more difficult. It has been found preferable to employ freshly prepared silver oxide for the reaction, since the material tends to lose its catalytic efficiency upon standing for prolonged periods. The silver oxide is prepared from silver nitrate using known procedures. The reaction may be carried out at from 10°–50° C., however, reaction at room temperature is preferred. The reaction generally requires from 2 to 10 days for completion. Reaction progress is monitored by taking aliquots from the reaction mixture and examining them with thin layer chromatographic techniques. Possible side reactions are avoided by carrying out the reaction in the dark, and this method is preferred. The product is isolated using techniques known to those skilled in the art.

In one modification of the Koenigs-Knorr reaction, known as the Helferich modification thereof, a mercuric halide, such as mercuric chloride or bromide, alone or in combination with mercuric oxide or mercuric cyanide is substituted for the silver oxide. The above described reaction conditions may be employed except that nitromethane and benzene are the preferred solvents and reflux temperature is the preferred reaction temperature.

The silver triflate reaction uses the reagent silver triflate (silver trifluoromethyl sulfonate) and the acetohalosugar in the same solvents listed above, with ether being preferred. The silver triflate is best if highly purified and prepared fresh just prior to its use. Methods for the preparation of silver triflate are well known to those skilled in the art. All of the reactants are combined in the solvent and the reaction conducted at from 10° to 50° C. for from 2 to 48 hours. Generally, however, the reaction is complete in about 24 hours at room temperature. The progress of the reaction may be followed by thin layer chromatography techniques. Again the reaction is preferably carried out in the dark, and with absolutely dry reactants and equipment.

A single mole of the sugar is required, however, a single molar excess is often used to aid in the course of the reaction.

During the course of the reaction a mole of triflic acid (trifluoromethanesulfonic acid) is liberated. This is a very strong acid and a molar equivalent of a base is required to neutralize the acid. Preferred bases are non-nucleophilic bases such as tertiary amines, preferably triethylamine, diisopropylethylamine, diazabicycloundecane, diazabcyclononane and the like. Since triflic acid is such as strong acid, if the base used is not a strong enough base to netutralize all of the acid, the residual acid will adversely affect the course of the reaction and of the isolation of the product. The product is isolated using techniques known to those skilled in the art.

The orthoester process prepares sugar derivatives of the milbemycin compounds from orthoesters of a lower alkanol and of the above sugars at the hydroxy function of said milbemycins. The ortho esters are prepared from the acetohalosugars using a loweralkanol and procedures which are well known to those skilled in the art. The reaction is carried out in an aprotic solvent such as dichloroethane, nitromethane, methylene chloride, dimethoxy ether, acetonitrile, tetrahydrofuran and the like. Dichloroethane, nitromethane, dimethoxy ethane and tetrahydrofuran are preferred. The reaction is preferably carried out at the reflux temperature of the reaction mixture and is generally complete in from about 4 to 24 hours. Catalytic amounts of mercuric bromide or mercuric chloride are added to aid in the reaction. During the course of the reaction one mole of the alcohol used to make the orthoester is liberated. Thus, the preferred method is to azeotropically distill off the solvent to remove the alcohol and to force the reaction to completion. To prevent any volume reduction, fresh solvent is added as the distillation proceeds to maintain a constant volume. To isolate the product, the solvent is generally removed and the residue washed with a reagent to remove the mercury salts, such as aqueous potassium iodide. The poduct is then isolated using known techniques.

Where there is more than one position with a hydroxy group which is susceptable to reaction (the 7-position tertiary hydroxy has been found to be less reactive toward substitution with a sugar moiety than the others), selective substitution may be obtained by careful ordering of the reaction steps. For example if the 13-hydroxy-5-glycosyloxy milbemycin $\alpha_1$ is desired, the sugar reactions may be carried out on the 13-unsubstituted milbemycin $\alpha_1$ and then the reactions required to prepare the 13-hydroxy may be carried out. Further glycosylation reactions may then be carried out on the 13-hydroxy-5-glycosyloxy milbemycin $\alpha_1$ to prepare a compound with different sugar groups at the 5- and 13-positions. Alternatively selective acylation of one of the hydroxy groups may be used to direct the glycosylation to another hydroxy group. If the 13-glycosyloxy milbemycin $\alpha_1$ is desired, the 5-hydroxy would be protected by acylation thereof, using known techniques and standard acylation reagents such as acid halides, anhydrides and the like. Then the 13-hydroxy group would be prepared and the glycosylation reactions carried out. The desired product would then be prepared by simple hydrolysis of the 5-acyl group.

Milbemycine $\alpha_6$ and $\alpha_8$ have hydroxy groups at the 22 and 13 positions and processes for selectively glycosylating these compounds would follow a procedure similar to that employed for glycosylating compounds at the 5 and 13 positions. The milbemycin $\alpha_5$ and $\alpha_7$ compounds have hydroxy groups at the 5,13 and 22 positions. The selectivity of the 5 and 22 positions has been found to be very similar, thus reactions under the foregoing conditions will produce a mixture of compounds with sugar moieties at the 5, the 22 and at both positions. chromatographic techniques have been found to be very useful in separating mixtures of these compounds. In this manner, any combination of compounds with more than one available hydroxy group may be selectively substituted with the above sugar moieties.

The following examples are provided in order that the reaction might be more fully understood. They should not be construed as limitative of the invention.

EXAMPLE 1

13-(2,3,4,6,-Tetra-O-acetyl-O-glucopyranosyloxy) milbemycin $\alpha_2$

To a solution of 13-hydroxy milbemycin $\alpha_2$ (280 mg.) in anhydrous ether (precautions are taken to insure anhydrous conditions of solvent and glassware) is added freshly prepared silver oxide (230 mg.) and then acetobromoglucose (410 mg.). The mixture is magnetically stirred at ambient temperature for 4 days in the dark. The solids are filtered and washed with ether and the volume of the filtrate is reduced in vacuo. The resulting solution is purified by column chromatography on silca gel using dichloromethane-methanol mixtures as eluant, affording 13-(2,3,4,6-tetra-O-acetyl-O-glucopyranosyloxy) milbemycin $\alpha_2$.

EXAMPLE 2

13-(D-glucopyranosyloxy) milbemycin $\alpha_2$

The acetylated glucopyranosyl derivative (50 mg.) of Example 1 is treated with sufficient methanolic ammonia (2 ml., presaturated at 0°) to cover the starting material, and the reaction is monitored by thin layer chromatography at one hour intervals. The reaction is complete in 6 hours and the solvent is removed in vacuo. The product purified by column chromatography using a dichloromethane-methanol mixture as eluant.

EXAMPLE 3

5-O-(2,3,4,6-Tetra-O-acetyl-$\beta$-O-glucopyranosyl) milbemycin $\alpha_1$

To a mixture of milbemycin $\alpha_1$ (560 mg.), acetobromoglucose (820 mg.) and diisopropylethylamine (260 mg.) in anhydrous ether (precautions are taken to insure anhydrous conditions of solvent and glassware) is added silver triflate (280 mg.). The mixture is stirred (magnetically) at ambient temperature in the dark until further reaction stops (as monitored by thin layer chromatography). 24 Hours reaction time is required. The solids are filtered, washed with ether and the filtrate is partitioned with aqueous dilute sodium bicarbonate, separated, washed with water, and dried over sodium sulfate. The solvent is removed in vacuo and the product is purified by column chromatography on silca gel using dichloromethane-methanol mixtures as eluant.

EXAMPLE 4

5-O-($\beta$-D-Glucopyranosyl) milbemycin $\alpha_1$

Following the procedure of Example 2, the peracetylated glucopyranosyl milbemycin $\alpha_1$ of Example 3 is treated with methanolic ammonia and the product 5-O-($\beta$-D-glucopyranosyl) milbemycin $\alpha_1$ isolated.

EXAMPLE 5

13-(2,3,4-tri-O-acetyl-$\alpha$-L-rhamnopyranosyloxy) milbemycin $\alpha_1$

To a solution of 13-hydroxy milbemycin $\alpha_1$ (250 mg.) in vigorously anhydrous dichloroethane is added 3,4-di-O-acetyl-1,2-methylorthoacetyl-$\beta$-L-rhamnopyranose (450 mg.) and mercuric bromide (360 mg.) The mixture is heated at reflux under nitrogen with slow removal of solvent (and formed methanol) by distillation. Solvent removed by distillation is replaced with fresh solvent from a dropping funnel. The reaction is monitored by thin layer chromatography and when it ceases to make further progress is cooled, washed with 30% aqueous potassium iodide, water and dried over sodium sulfate. Column chromatography using chloroform-methanol mixtures as eluants resolves the glycosidic products. After lyophilization from benzene the product 13-(2,3,4-tri-O-$\alpha$-L-rhamnopyranosyloxy) milbemycin $\alpha_1$ is isolated as an amorphous solid.

EXAMPLE 6

13-($\alpha$-L-rhamnopyranosyloxy) milbemycin $\alpha_1$

Following the procedure of Example 2 using the product of Example 5 as starting material, there is obtained 13-($\alpha$-L-rhamnopyranosyloxy) milbemycin $\alpha_1$.

EXAMPLE 7

13-(L-oleandrosyl-$\alpha$-L-oleandrosyl)-milbemycin $\alpha_1$

The procedure of Example 1 is followed employing 100 mg. of 5-O-acetyl-13-hydroxy milbemycin $\alpha_1$ in place of 13-hydroxy milbemycin $\alpha_2$ and 250 mg. of 4-O-acetyl-$\alpha$-L-oleandrosyl-L-oleandrosyl-L-oleandrosyl chloride in place of acetobromoglucose. (The halogenose is also known as 4-O(4-O-acetyl-2,6-dideoxy-3-O-methyl-$\alpha$-L-lyxo-hexopyranosyl)-2,6-dideoxy-3-O-methyl-L-lyxo-hexopyranosyl chloride). The product is purified using preparative layer chromatography affording 13-(4-O-acetyl-$\alpha$-L-oleandrosyl-L-oleandrosyl)-5-O-acetyl-milbemycin $\alpha_1$.

The above compound is hydrolyzed according to the procedures of Example 2, affording 13-(L-oleandrosyl-$\alpha$-L-oleandrosyl) milbemycin $\alpha_1$.

EXAMPLE 8

5-O-Acetyl-22-(4-O-Acetyl-$\alpha$-L-Oleandrosyl-$\alpha$-L-oleandrosyloxy) Milbemycin $\alpha_6$ A solution of 100 mg. of milbemycin $\alpha_6$ is treated with 250 mg. of 4-O-acetyl-$\alpha$-L-oleandrosyl-L-oleandrosyl chloride (also named as 4-O-(4-O-acetyl-2,6-dideoxy-3-O-methyl-$\alpha$-L- lyxo hexopyranosyl)-2,6-dideoxy-3-O-methyl-L- ;yxo hexopyranosyl chloride) following the procedure of Example 3. The product 22-(4-O-acetyl-$\alpha$-L-oleandrosyl-$\alpha$-L-oleandrosyloxy) milbemycin $\alpha_6$ is isolated and purified on preparative layer chromatography plates using methylene chloride methanol mixtures as solvent.

EXAMPLE 9

22-(4-O-Acetyl-$\alpha$-L-Oleandrosyl-$\alpha$-L-oleandrosyloxy) Milbemycin $\alpha_6$ The product of Example 8 is hydrolized following the procedure of Example 2 to produce 22-($\alpha$-L-oleandrosyl-$\alpha$-L-oleandrosyloxy) milbemycin $\alpha_6$.

PREPARATIONS

A. 13-Bromo milbemycin $\alpha_2$

A solution of 542 mg. of milbemycin $\alpha_2$ and 178 mg. of N-bromosuccinimide in 10 ml. of carbon tetrachloride is stirred under irradiation with ultraviolet light for 1 hour at room temperature. The mixture is cooled to 0° C., the succinimide is filtered off and the solvent is removed by evaporation under reduced pressure. Chromatography of a solution of the residue in a mixture of chloroform and tetrahydrofuran (95:5) over a column of silica yields 13-bromo milbemycin $\alpha_2$.

B. 13-Acetoxy milbemycin $\alpha_2$

A solution of 621 mg. of 13-bromo milbemycin $\alpha_2$ and 82 mg. of anhydrous sodium acetate in 10 ml. of acetic acid is stirred for 24 hours at 20° C. -30° C. The acetic acid is evaporated under reduced pressure and the product is separated from the sodium bromide by extraction with ether and evaporation. Chromatography of the product extracted into the ether in a mixture of chloroform and tetrahydrofuran (95:5) over a column of silica yields 13-acetoxy milbemycin $\alpha_2$.

C. 13-Hydroxy milbemycin $\alpha_2$

A solution of 600 mg. of 13-acetoxy milbemycin $\alpha_2$ and 44 mg. of sodium hydroxide in a mixture of 8 ml. of methanol and 2 ml. of water is stirred for 10 hours at 0°-10° C. The solvent is evaporated under reduced pressure and the residue is dissolved in chloroform. Chromatography of the chloroform solution over a column of silica yields 13-hydroxy milbemycin $\alpha_2$.

Other milbemycin compounds such as $\alpha_3$, $\alpha_4$, $\alpha_5$, $\alpha_6$, $\alpha_7$, $\alpha_8$, $\alpha_9$, $\alpha_{10}$, $\beta_1$, $\beta_2$ and $\beta_3$ may be similarly converted into the 13-hydroxy derivatives either before or after the sugar reactions described above.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichlostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris.

Certain of these, such as Nematodirus, cooperia, and Oesophagostomum attack primarily the intestinal tract while others, such as Haemonchus and Ostertagia, are more prevalent in the stomach, while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The milbemycin derivatives of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostroma, necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the milbemycin derivatives in a dry, solid unit dosage form, capsules, boluses or tablets containing the desired amount Ancylostoma, Necator, compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active milbemycin compound or compounds are dissolved or suspended in the parenteral formulation for administration; such formulations generally contain from 0.005 to 5% by weight of the active compound.

What is claimed is:

1. A compound having the formula:

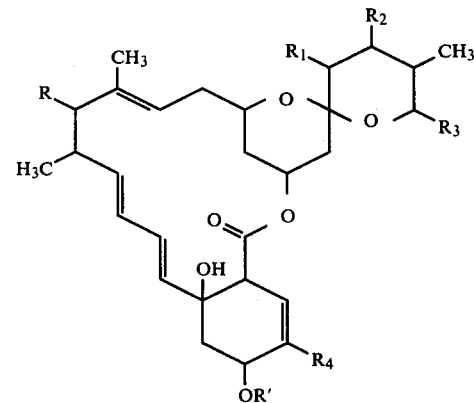

wherein R is hydrogen or a sugar moiety and $R_1$, $R_2$, $R_3$ and R' are defined as follows:

| $R_1$ | $R_2$ | $R_3$ | $R_4$ | R' |
|---|---|---|---|---|
| H | H | $CH_3$ | $CH_3$ | H or sugar |
| H | H | $CH_3$ | $CH_3$ | $CH_3$ |
| H | H | $C_2H_5$ | $CH_3$ | H or sugar |
| H | H | $C_2H_5$ | $CH_3$ | $CH_3$ |
| —OH or sugar | $-O-\overset{O}{\overset{\|}{C}}-\overset{CH_3}{\overset{\|}{C}HC_4H_9}$ | $CH_3$ | $CH_3$ | H or sugar |
| —OH or sugar | $-O-\overset{O}{\overset{\|}{C}}-\overset{CH_3}{\overset{\|}{C}H-C_4H_9}$ | $CH_3$ | $CH_3$ | $CH_3$ |
| —OH or sugar | $-OC-\overset{O}{\overset{\|}{C}}H-\overset{CH_3}{\overset{\|}{C_4H_9}}$ | $C_2H_5$ | $CH_3$ | H or sugar |
| —OH or sugar | $-OC-\overset{O}{\overset{\|}{C}}H-\overset{CH_3}{\overset{\|}{C_4H_9}}$ | $C_2H_5$ | $CH_3$ | $CH_3$ |
| H | H | $CH_3$ | $-CH_2O\overset{O}{\overset{\|}{C}}-\langle{}_N{}\rangle$ | H or sugar |

-continued

| $R_1$ | $R_2$ | $R_3$ | $R_4$ | $R'$ |
|---|---|---|---|---|
| H | H | $CH_3$ | $-CH_2OC(=O)\text{-pyrrole}$ | H or sugar | or

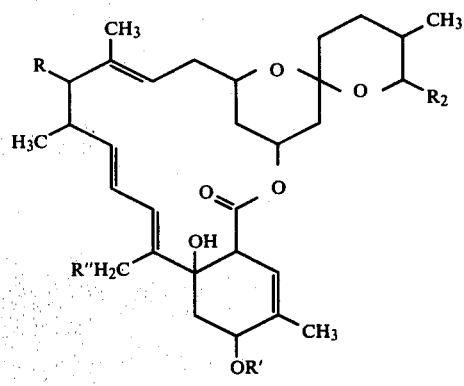

wherein R is hydrogen or a sugar moiety and $R_2$, $R'$ and $R''$ are defined as follows:

| $R_2$ | $R'$ | $R''$ |
|---|---|---|
| $CH_3$ | $CH_3$ | —OH or —O-sugar |
| $C_2H_5$ | $CH_3$ | —OH or —O-sugar |
| $CH_3$ | H or sugar | H | provided that in the first of the above structural formulae at least one of R, $R_1$ and $R'$ is a sugar moiety and in the second of the above structural formulae at least one of R, $R'$, and $R''$ is or contains a sugar moiety, wherein said sugar moiety is a mono, di- or trisaccharide selected from glucopyranosyl, galactopyranosyl, mannopyranosyl, maltosyl, arabinopyranosyl, lyxopyranosyl, xylopyranosyl, ribopyranosyl, oleandrosyl, rhamnopyranosyl, fucopyranosyl, lactosyl, ribofuranosyl, mannofuranosyl, glucofuranosyl, arabinofuranosyl, mycarosyl, cladinosyl, desosaminosyl, daunosaminosyl, mycaminosyl.

2. The compounds of claim 1 wherein the sugar is a mono or disaccharide selected from glucopyranosyl, rhamnopyranosyl, oleandrosyl and daunosaminosyl.

3. The compound of claim 2 wherein the sugar is a mono or disaccharide selected from glucopyranosyl and oleandrosyl.

4. A compound of claim 3 which is 13-($\beta$-D-glucopyranosyloxy) milbemycin $\alpha_2$.

5. A compound of claim 3 which is 5-O-($\beta$-D-glucopyranosyl) milbemycin $\alpha_1$.

6. The compound of claim 3 wherein the sugar is L-oleandrosyl-$\alpha$-L-oleandrosyl.

7. A compound of claim 6 which is 13-(L-oleandrosyl-$\alpha$-L-oleandrosyl) milbemycin $\alpha_1$.

8. A compound of claim 6 which is 5-O-(L-oleandrosyl-$\alpha$-L-oleandrosyl) milbemycin $\alpha_1$.

9. A compound of claim 6 which is 13-(L-oleandrosyl-$\alpha$-L-oleandrosyl) milbemycin $\alpha_2$.

10. A method for the treatment of parasitic infections, which comprises administering to an animal infected with parasites an effective amount of a compound of claim 1.

* * * * *